US009930908B2

(12) United States Patent
Greenberg et al.

(10) Patent No.: US 9,930,908 B2
(45) Date of Patent: Apr. 3, 2018

(54) HIGH PROTEIN NUTRITIONAL COMPOSITIONS AND METHODS OF MAKING AND USING SAME

(75) Inventors: Norman Alan Greenberg, New Hope, MN (US); Doug Bolster, Lake In The Hills, IL (US); Zamzam Kabiry (Fariba) Roughead, Plymouth, MN (US)

(73) Assignee: Nestec S.A., Vevey (CH)

( * ) Notice: Subject to any disclaimer, the term of this patent is extended or adjusted under 35 U.S.C. 154(b) by 814 days.

(21) Appl. No.: 13/982,822

(22) PCT Filed: Jan. 26, 2012

(86) PCT No.: PCT/US2012/022726
§ 371 (c)(1),
(2), (4) Date: Oct. 14, 2013

(87) PCT Pub. No.: WO2012/106179
PCT Pub. Date: Aug. 9, 2012

(65) Prior Publication Data
US 2014/0308390 A1 Oct. 16, 2014

Related U.S. Application Data

(60) Provisional application No. 61/438,804, filed on Feb. 2, 2011.

(51) Int. Cl.
| | | |
|---|---|---|
| *A23L 1/29* | (2006.01) | |
| *A23L 33/00* | (2016.01) | |
| *A23L 33/115* | (2016.01) | |
| *A23L 33/17* | (2016.01) | |

(52) U.S. Cl.
CPC .............. *A23L 33/40* (2016.08); *A23L 33/115* (2016.08); *A23L 33/17* (2016.08)

(58) Field of Classification Search
CPC ......... A23L 1/296; A23L 1/305; A23L 1/3006
See application file for complete search history.

(56) References Cited

U.S. PATENT DOCUMENTS

| | | | |
|---|---|---|---|
| 6,140,304 A | 10/2000 | Sears | |
| 2004/0121044 A1* | 6/2004 | Tiano et al. | 426/72 |
| 2005/0054724 A1 | 3/2005 | Mustad et al. | |

FOREIGN PATENT DOCUMENTS

| | | |
|---|---|---|
| CN | 1700862 | 11/2005 |
| EP | 1665940 | 6/2006 |
| JP | 2002523356 | 7/2002 |
| JP | 2004526730 | 9/2004 |
| JP | 2009506012 | 2/2009 |
| WO | 2004017764 | 3/2004 |
| WO | 2006002976 | 1/2006 |
| WO | 2008001086 | 1/2008 |

OTHER PUBLICATIONS

Gibson et al., (1995) "Dietary Modulation of the Human Colonic Microbiota: Introducing the Concept of Prebiotics" J. Nutr 125:1401-1412.
Salminen et al., "Probiotics: how should they be defined?." Trends in food science & technology 10.3 (1999): 107-110.
PCT International Search Report for Application No. PCT/US2012/022726 dated May 3, 2012—3 Pages.
PCT Written Opinion of the PCT International Searching Authority for Application No. PCT/US2012/022726 dated May 3, 2012—5 Pages.
IPRP for Application No. PCT/US2012/022726 dated Aug. 6, 2013—1 Page.
Office Action issued in CN Application 201280007307.3, dated Mar. 26, 2015. 16 pages.
Article—"Fish, Catfish, Channel, Farmed, Raw" Self Nutrition Data, Know What You Eat, WaybackMachine, Published Dec. 2, 2010, From the Internet at http://web.archive.org/web/20101202091648/http:/nutritiondata.self.com/facts/finfish-and-shellfish-products/4256/2, Printed May 7, 2015, 2 pages.
Simopoulos "Omega-6/Omega-3 Essential Fatty Acid Ratio and Chronic Diseases" Food Reviews International, 2004, vol. 20, No. 1, pp. 77-90.
Hainer et al. "Composition of a low-energy protein diet for the treatment of obesity" Ceskoslovenska Gastroenterologie a Vyziva, 1990, vol. 44, No. 3, pp. 173-180.
Okajima et al. "Usefulness of a high protein, low energy nutrition diet "Panaprocky" in the treatment of obesity" the Japanese Journal of Clinical Nutrition, 1993, vol. 83, No. 5, pp. 649-652.
Ailhaud et al. "An emerging risk factor for obesity: does disequilibrium of polyunsaturated fatty acid metabolism contribute to excessive adipose tissue development?" British Journal of Nutrition, 2008, vol. 100, pp. 461-470.
Abete et al. "Obesity and the metabolic syndrome: role of different dietary macronutrient distribution patterns and specific nutritional components on weight loss and maintenance" Nutrition Reviews, vol. 68, No. 4, pp. 214-231.
Japanese Office Action for Application No. P2013-552560, Dispatch No. 397903, dated Sep. 1, 2015, 11 pages.

* cited by examiner

*Primary Examiner* — Elizabeth Gwartney
(74) *Attorney, Agent, or Firm* — K & L Gates LLP

(57) ABSTRACT

Nutritional compositions having high amounts of protein and low ratios of omega-6:omega-3 fatty acids, and methods of making and using the nutritional compositions are provided. The nutritional compositions include an increased amount of protein, and a low ratio of omega-6:omega-3 fatty acids to provide a patient with adequate amounts of protein for the preservation of lean body mass, while reducing inflammation associated with administration of pro-inflammatory drug formulations such as propofol. The nutritional compositions also help to avoid potential complications associated with overfeeding of an enterally-fed patient being treated, or having been treated, with high fat medications such as propofol. Methods of making and using such nutritional compositions are also provided.

4 Claims, No Drawings

HIGH PROTEIN NUTRITIONAL COMPOSITIONS AND METHODS OF MAKING AND USING SAME

CROSS REFERENCE TO RELATED APPLICATIONS

The present application is a National Stage of International Application No. PCT/US2012/022726, filed on Jan. 26, 2012, which claims priority to U.S. Provisional Patent Application No. 61/438,804, filed Feb. 2, 2011, the entire contents of which are being incorporated herein by reference.

BACKGROUND

The present disclosure generally relates to health and nutrition. More specifically, the present disclosure relates to nutritional compositions having a high amount of protein to provide patients with an adequate amount of protein while avoiding potential complications of overfeeding. Methods of making and using the nutritional compositions are also provided.

There are many types of nutritional compositions currently on the market. Nutritional compositions can be targeted toward certain consumer types, for example, young, elderly, athletes, and also those suffering from chronic or acute conditions or illnesses, etc., based on the specific ingredients of the nutritional composition. Nutritional compositions can also be formulated based on the certain physiological conditions that the nutritional compositions are intended to manage, treat or improve.

One goal of nutritional support is to provide enough daily amounts of protein to preserve lean body mass, but to also reduce complications associated with overfeeding of enterally fed patients. For example, while modular products such as protein supplements are appropriate for some patients and serve a useful purpose, other patients may not be appropriate recipients of modular supplements due to a need to restrict total fluid volume, or fat intake, each day. Further, existing high protein formulas provide up to 25% of the energy as protein. To provide an adequate daily amount of protein, several protein modulars of this type must be administered per day. Each modular unit requires that the feeding tube be flushed clear with water, administered, and then the tube flushed again. This can cause an excessive amount of fluid to be administered to patients. Administering a plurality of modulars, which may be high in fat content, may also mean that the patient may be administered excessive amounts of fat.

As such, it would be beneficial to provide a sufficient amount of protein to a patient while avoiding any overfeeding complications that may be associated with the administration of several modulars per day.

SUMMARY

Nutritional compositions having increased amounts of protein and low ratios of omega-6:omega-3 fatty acids are provided. Methods of making and using the nutritional compositions are also provided. In a general embodiment, the present disclosure provides nutritional compositions including at least 30% of its energy as protein, at least one fish oil, and a low ratio of omega-6 to omega-3 fatty acids. In an embodiment, the source of protein provides protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In another embodiment, nutritional compositions are provided that include a source of protein that provides protein in an amount from about 50 g to about 200 g per 1500 kcal, and an omega-6 to omega-3 fatty acid ratio from about 1.0:0.5 to about 2.5:1.5. The source of protein may provide protein in an amount from about 75 g to about 150 g per 1500 kcal. The source of protein may also protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In an embodiment, the protein is selected from the group consisting of dairy based proteins, plant based proteins, animal based proteins, artificial proteins, or combinations thereof. The dairy based proteins may be selected from the group consisting of casein, casein hydrolysates, caseinates, whey, whey hydrolysates, milk protein concentrate, milk protein isolate, or combinations thereof. The plant based proteins may be selected from the group consisting of soy protein, pea protein, canola protein, wheat and fractionated wheat proteins, corn proteins, zein proteins, rice proteins, oat proteins, potato proteins, peanut proteins, green pea powder, green bean powder, proteins derived from beans, lentils, and pulses, or combinations thereof.

In an embodiment, the nutritional composition includes fiber or a source of fiber. The fiber may be a prebiotic selected from the group consisting of acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof In an embodiment, the nutritional composition includes a probiotic selected from the group consisting of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

In an embodiment, the nutritional composition includes an amino acid selected from the group consisting of alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof In an embodiment, the nutritional composition includes a fish oil selected from the group consisting of docosahexaenoic acid, eicosapentaenoic acid, or combinations thereof. The nutritional compositions may include fish oil and a source of fatty acids that provide the nutritional composition with a ratio of omega-6:omega-3 fatty acids from about 1.0:0.5 to about 2.5:1.5. In an embodiment, the nutritional compositions have a ratio of omega-6:omega-3 fatty acids of about 1.8:1.0.

In an embodiment, the nutritional composition includes a phytonutrient selected from the group consisting of flavanoids, allied phenolic compounds, polyphenolic compounds, terpenoids, alkaloids, sulphur-containing compounds, or combinations thereof. The phytonutrient may be, for example, a carotenoids, plant sterols, quercetin, curcumin, or limonin, or combinations thereof.

In an embodiment, the nutritional composition includes a nucleotide. The nucleotide may be a subunit of deoxyribonucleic acid, a subunit of ribonucleic acid, or combinations thereof In an embodiment, the nutritional composition includes an antioxidant selected from the group consisting of carotenoids, coenzyme Q10 ("CoQ10"), flavonoids, glutathione Goji (wolfberry), hesperidine, lactowolfberry, lignan, lutein, lycopene, polyphenols, selenium, vitamin A, vitamin $B_1$, vitamin $B_6$, vitamin $B_{12}$, vitamin C, vitamin D, vitamin E, or combinations thereof.

In an embodiment, the nutritional composition includes vitamins selected from the group consisting of vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid, biotin, choline, or combinations thereof.

In an embodiment, the nutritional composition includes minerals selected from the group consisting of boron, calcium, chromium, copper, iodine, iron, magnesium, manganese, molybdenum, nickel, phosphorus, potassium, selenium, silicon, tin, vanadium, zinc, or combinations thereof.

In another embodiment, the present disclosure provides methods of making a nutritional composition. The methods include combining a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5 to form a mixture; and mixing the mixture to form the nutritional composition. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In yet another embodiment, the present disclosure provides methods of making a nutritional composition. The methods include combining a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5 to form a mixture, and mixing the mixture to form the nutritional composition. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In yet another embodiment, methods of treating a patient suffering from, or at risk of suffering from, complications associated with excessive feeding are provided. The methods include administering to a patient suffering from, or at risk of suffering from excessive feeding, a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In still yet another embodiment, methods of treating a patient suffering from, or at risk of suffering from, complications associated with excessive feeding are provided. The methods include administering to a patient suffering from, or at risk of suffering from excessive feeding, a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In another embodiment, methods of treating and/or preventing obesity in an enterally-fed patient are provided. The methods include administering to an obese patient, or a patient at risk of becoming obese, a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In yet another embodiment, methods of treating and/or preventing obesity in an enterally-fed patient are provided. The methods include administering to an obese patient, or a patient at risk of becoming obese, a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In still yet another embodiment, methods of reducing healthcare costs for a patient are provided. The methods include providing a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In yet another embodiment, methods of reducing healthcare costs for a patient are provided. The methods include providing a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In an embodiment, the reduction in costs is due to at least one of a reduced gastroparesis, reduced risk of ileus, reduced bacterial overgrowth, reduced bacterial translation, decreased infections, decreased $CO_2$ production, decreased time on a ventilator, decreased metabolic acidosis, decreased respiratory acidosis, decreased ventilator weaning time, reduced hypotension, decreased length of stay in a healthcare clinic or hospital, decreased healthcare costs, decreased labor time for healthcare professionals, and decreased liver toxicities.

In still yet another embodiment, methods of reducing inflammation caused by administration of propofol to a patient are provided. The methods include providing a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In yet another embodiment, methods of reducing inflammation caused by administration of propofol to a patient are provided. The methods include providing a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In another embodiment, methods of avoiding overfeeding of patients being treated with, or having been treated with, a high fat medication, are provided. The methods include providing a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In yet another embodiment, methods of avoiding overfeeding of patients being treated with, or having been treated with, a high fat medication, are provided. The methods include providing a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In still yet another embodiment, methods of reducing fat intake of patients being treated with, or having been treated with, a high fat medication, are provided. The methods include providing a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In another embodiment, methods of reducing fat intake of patients being treated with, or having been treated with, a high fat medication, are provided. The methods include providing a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In another embodiment, methods of providing a balanced daily fat intake to patients being treated with, or having been treated with, a high fat medication, are provided. The methods include providing a nutritional composition comprising a source of protein that provides protein in an amount of at least 30% of the total energy of the nutritional composition, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount of at least 35% of the total energy of the nutritional composition. The source of protein may also provide protein in an amount of about 37% of the total energy of the nutritional composition. The ratio of omega-6:omega-3 fatty acids may be about 1.8:1.0.

In yet another embodiment, methods of providing a balanced daily fat intake to patients being treated with, or having been treated with, a high fat medication, are provided. The methods include providing a nutritional composition comprising a source of protein that provides protein in an amount from about 50 g to about 200 g per 1500 kcal, and at least one source of fatty acids that provides the nutritional composition with an omega-6 to omega-3 fatty acid ratio from about 1.0:0.5 to about 2.5:1.5, and administering the nutritional composition to the patient. The source of protein may provide protein in an amount from about 75 g to about 150 g per 1500 kcal. The source of protein may also provide protein in an amount of about 140 g per 1500 kcal. The source of protein may provide protein in an amount from about 100 g to about 150 g per 1150 kcal. The source of protein may provide protein in an amount of about 106 g per 1150 kcal. The ratio of omega-6:omega-3 fatty acids may be about 1.8:1.0.

In an embodiment, the high fat medication is propofol, and the patient is a mechanically ventilated patient. The patient may also be fed enterally and the nutritional composition may provide a balanced daily fat intake.

The compositions and methods of the present disclosure may further include adding to the nutritional compositions a fish oil selected from the group consisting of docosahexaenoic acid, eicosapentaenoic acid, or combinations thereof An advantage of the present disclosure is to provide improved nutritional compositions.

Another advantage of the present disclosure is to provide improved nutritional compositions that comprise increased amounts of protein.

Yet another advantage of the present disclosure is to provide nutritional compositions that preserve lean body mass.

Still yet another advantage of the present disclosure is to provide nutritional compositions that avoid complications associated with overfeeding.

Another advantage of the present disclosure is to provide nutritional compositions that decrease healthcare costs.

Yet another advantage of the present disclosure is to provide nutritional compositions that decrease carbon dioxide production.

An advantage of the present disclosure is to provide nutritional compositions that reduce bacterial translation and overgrowth.

Still yet another advantage of the present disclosure is to provide nutritional compositions that reduce inflammation.

Additional features and advantages are described herein, and will be apparent from the following Detailed Description and the figures.

DETAILED DESCRIPTION

The present disclosure is directed to nutritional compositions having increased amounts of protein and low ratios of omega-6:omega-3 fatty acids, and method of making and using same. The nutritional compositions can be used for the preservation of lean body mass and to avoid any complications associate with overfeeding including, for example, elevated dietary fat levels, liver toxicities, bacterial overgrowth, etc.

As used in this disclosure and the appended claims, the singular forms "a," "an" and "the" include plural referents unless the context clearly dictates otherwise. Thus, for example, reference to "an amino acid" includes a mixture of two or more amino acids, and the like.

As used herein, "about" is understood to refer to numbers in a range of numerals. Moreover, all numerical ranges herein should be understood to include all integer, whole or fractions, within the range. All dosage ranges contained within this application are intended to include all numbers, whole or fractions, contained within said range.

As used herein the term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (wolfberry), hesperidine, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

As used herein, "effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

While the terms "individual" and "patient" are often used herein to refer to a human, the present disclosure is not so limited. Accordingly, the terms "individual" and "patient" refer to any animal, mammal or human having or at risk for a medical condition that can benefit from the treatment.

As used herein, non-limiting examples of fish oils include docosahexaenoic acid ("DHA") and eicosapentaenoic acid ("EPA"). DHA and EPA may also be present from a non-fish oil source (e.g., algae, modified plants, etc.).

As used herein, "food grade micro-organisms" means micro-organisms that are used and generally regarded as safe for use in food.

As used herein, "long term administrations" are continuous administrations for more than 6 weeks As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof "Nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein, "phytochemicals" or "phytonutrients" are non-nutritive compounds that are found in many foods. Phytochemicals are functional foods that have health benefits beyond basic nutrition, and are health promoting compounds that come from plant sources. As used herein, "Phytochemicals" and "Phytonutrients" refers to any chemical produced by a plant that imparts one or more health benefit on the user. Phytochemicals can be administered by any means, including topically, enterally, and/or parenterally. As used herein, non-limiting examples of phytochemicals and phytonutrients include those that are i) Phenolic compounds which include Monophenols (such as: Apiole, Carnosol, Carvacrol, Dillapiole, Rosemarinol); Flavonoids (polyphenols) including Flavonols (such as: Quercetin, Gingerol, Kaempferol, Myricetin, Rutin, Isorhamnetin), Flavanones (such as: Hesperidin, Naringenin, Silybin, Eriodictyol), Flavones (such as: Apigenin, Tangeritin, Luteolin), Flavan-3-ols (such as: Catechins, (+)-Catechin, (+)-Gallocatechin, (−)-Epicatechin, (−)-Epigallocatechin, (−)-Epigallocatechin gallate (EGCG), (−)-Epicatechin 3-gallate, Theaflavin, Theaflavin-3-gallate, Theaflavin-3'-gallate, Theaflavin-3,3'-digallate, Thearubigins), Anthocyanins (flavonals) and Anthocyanidins (such as: Pelargonidin, Peonidin, Cyanidin, Delphinidin, Malvidin, Petunidin), Isoflavones (phytoestrogens) (such as: Daidzein (formononetin), Genistein (biochanin A), Glycitein), Dihydroflavonols, Chalcones, Coumestans (phytoestrogens), and Coumestrol; Phenolic acids (such as: Ellagic acid, Gallic acid, Tannic acid, Vanillin, Curcumin); Hydroxycinnamic acids (such as: Caffeic acid, Chlorogenic acid, Cinnamic acid, Ferulic acid, Coumarin); Lignans (phytoestrogens), Silymarin, Secoisolariciresinol, Pinoresinol and lariciresinol); Tyrosol esters (such as: Tyrosol, Hydroxytyrosol, Oleocanthal, Oleuropein); Stilbenoids (such as: Resveratrol, Pterostilbene, Piceatannol) and Punicalagins; ii) Terpenes (isoprenoids) which include Carotenoids (tetraterpenoids) including Carotenes (such as: α-Carotene, β-Carotene, γ-Carotene, δ-Carotene, Lycopene, Neurosporene, Phytofluene, Phytoene), and Xanthophylls (such as: Canthaxanthin, Cryptoxanthin, Zeaxanthin, Astaxanthin, Lutein, Rubixanthin); Monoterpenes (such as: Limonene, Perillyl alcohol); Saponins; Lipids including: Phytosterols (such as: Campesterol, beta Sitosterol, gamma sitosterol, Stigmasterol), Tocopherols (vitamin E), and omega-3, 6, and 9 fatty acids (such as: gamma-linolenic acid); Triterpenoid (such as: Oleanolic acid, Ursolic acid, Betulinic acid, Moronic acid); iii) Betalains which include Betacyanins (such as: betanin, isobetanin, probetanin, neobetanin); and Betaxanthins (non glycosidic versions) (such as: Indicaxanthin, and Vulgaxanthin); iv) Organosulfides which include Dithiolthiones (isothiocyanates) (such as: Sulphoraphane); and Thiosulphonates (allium compounds) (such as: Allyl methyl trisulfide, and Diallyl sulfide), Indoles, glucosinolates which include Indole-3-carbinol; sulforaphane; 3,3'-Diindolylmethane; Sinigrin; Allicin; Alliin; Allyl isothiocyanate; Piperine; Syn-propanethial-S-oxide; v) Protein inhibitors which include protease inhibitors; vi) Other organic acids which include Oxalic acid, Phytic acid (inositol hexaphosphate); Tartaric acid; and Anacardic acid; or combinations thereof.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125: 1401-1412. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y. et al., "Probiotics: how should they be defined?" Trends Food Sci. Technol. 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fuso-*

*bacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

The terms "protein," "peptide," "oligopeptides" or "polypeptide," as used herein, are understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present disclosure include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of proteins include dairy based proteins, plant based proteins, animal based proteins and artificial proteins. Dairy based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses.

As used herein, "short term administrations" are preferably continuous administrations for less than 6 weeks As used herein, a "synbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein, a "tube feed" is a complete or incomplete nutritional product or composition that is administered to an animal's gastrointestinal system, other than through oral administration, including but not limited to a nasogastric tube, orogastric tube, gastric tube, jejunostomy tube ("J-tube"), percutaneous endoscopic gastrostomy ("PEG"), port, such as a chest wall port that provides access to the stomach, jejunum and other suitable access ports.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid and biotin) essential in minute amounts for normal growth and activity of the body and obtained naturally from plant and animal foods or synthetically made, pro-vitamins, derivatives, analogs.

Patients may require specific nutritional compositions for a variety of reasons. For example, a patient may experience some form of trauma that requires mechanical ventilation and/or confinement to a bed and/or inability to ingest certain foods. In certain cases, the patient may require a special diet to provide proper nutrition to the patient, and may also require special administration of the nutritional compositions. Routes of administration are usually classified by application location and are distinguished from each other based on whether the effect of the administered composition is local (e.g., "topical" administration) or systemic (e.g., "enteral" or "parenteral" administration). Enteral administration is used to describe the intestines or other portions of the digestive tract. It includes oral, rectal, and sublingual administration as a route of administration for drugs/formulations. Parenteral administration, or non-digestive administration, includes methods of introducing drugs or substances into the body, via, for example, injection.

Many mechanically ventilated patients receive drugs for sedation purposes. One of the most extensively used drugs for this purpose is propofol. Propofol (marketed as Diprivan® by AstraZeneca) is not water soluble and, as a result, is a high fat, lipid-soluble drug that is required to be diluted in an emulsion (e.g., lipid and water) with elevated amounts of omega-6 fatty acids (e.g., linoleic acid, arachidonic acid, gamma-linolenic acid, etc.). The omega-6 fatty acids may be provided by the use of soybean oil in the propofol emulsion. Propofol typically contains about 0.1 g/ml of soybean oil, which has a ratio of omega-6:omega-3 fatty acids of about 7:1. Thus, this oil has a pro-inflammatory omega-6:omega-3 fatty acid ratio. The use of propofol, for example, for ventilated, enterally-fed patients can cause several health complications including, for example, decreased administration of protein, decrease of lean body mass, increased lower oesophageal sphincter ("LOS") pressure, increased rehabilitation time, and complications associated with overfeeding (e.g., increased fat intake from high fat medications). When propofol is used together with enteral nutrition, the total calories offered by the enteral route is required to be adjusted to compensate for the calories offered parenterally and, therefore, less eicosapentanoic ("EPA") and gamma linoleic acid ("GLA") are offered to the patient.

A recommended daily caloric intake for patients is about 1500 kcal/d. Because of the composition of a propofol emulsion, it is important to monitor the daily nutritional and energy intake of patients. For example, one recent report showed that ventilator patients sedated with propofol received, on average, about 350 kcal/d. See, Pontes-Arruda, "Influence of Propofol Sedation in the Benefits of EPA+ GLA Nutrition for the Treatment of Severe Sepsis," Crit. Care Med., Vol. 37, No. 12 (2009). Thus, about 23% of the caloric goal for the patient is achieved with the propofol lipid emulsion. If an obese or non-obese patient is sedated with propofol, then the reduction in feeding may be necessary to avoid overfeeding complications such as, but not limited to, hyperlipidemia, azotemia, hyperglycemia, fluid overload, hepatic dysfunction, and respiratory compromise. As such, it is evident that high fat medications such as, but not limited to, propofol can be a major cause of overfeeding with many enteral foods. No product on the market currently provides a high enough level of protein to provide the patient with adequate protein, while at the same time avoiding the potential complications associated with overfeeding (e.g., providing a beneficial fat balance to an enterally-fed patient).

For example, an enteral product of the prior art that provides protein in an amount of about 25% of the total energy and contains about 72 g protein in about 1150 kcal is not capable of providing adequate amounts of protein, while avoiding complications of overfeeding and reducing inflammation due to the pro-inflammatory fatty acid content of propofol. Indeed, excessive inflammation increases insulin resistance, which further reduces the anabolic effect of exogenous protein. Thus, the prior art products, even those promoted as high in protein, do not deliver enough protein to satisfy the needs of the vast majority of enterally-fed patients.

Inadequate dietary levels of protein can cause several undesirable health complications. For example, a lack of protein causes an increase in loss of lean body mass, as mentioned above. A loss of lean body mass can increase bacterial translocation due to a damaged GI tract. This, in turn, can increase the number of infections, which means additional usage of antibiotics that can further disrupt the gut microbiota. Antibiotic usage is also a significant cause of diarrhea, which damages the mucosa and necessitates the need to provide more protein for repair of the mucosa.

Many critical care patients are also now treated with dialysis on a more continuous basis. A high degree of dialysis can also cause an increase in protein loss. As such, patients undergoing continuous or near continuous dialysis should be administered compositions having adequate amounts of protein needed to replace the high levels of protein lost during dialysis.

As discussed above, a lack of adequate amounts of dietary protein can cause several complications associated with overfeeding in order to administer adequate amounts of protein to patients. Several of the complications include, for example, hyperlipidemia, azotemia, hyperglycemia, fluid overload, hepatic dysfunction and respiratory compromise. With respect to hyperlipidemia, the administration of high levels of fat for energy can lead to metabolic acidosis. One of the causes of metabolic acidosis is the consumption of a diet high in fat and low in carbohydrate. Interestingly, metabolic acidosis can cause shallow breathing, which can contribute to a delay in weaning from a ventilator. Further, excessive retention of carbon dioxide ("$CO_2$") is a primary cause of respiratory acidosis.

Excessive feeding can also cause an increase in $CO_2$ production, which can lead to a delay in weaning from a ventilator. In general, the more days that a patient is required to use a ventilator, the more days the patient will likely be administered propofol, which perpetuates the problem of excessive calorie intake due to the calories needed to provide this sedative. As a result, healthcare costs can be dramatically increased due to the increased time that the patient is hooked-up to the ventilator, and due to the increased time for rehabilitation.

Failure to ingest adequate amounts of dietary protein, and the resulting loss of lean body mass can also cause insulin resistance. Obese patients and diabetic patients are just two types of patients that generally have an increase in oxidative stress. Insulin resistance during metabolic stress can further cause patients to have a similar oxidative stress with hypermetabolism, and the formation of free radicals can impair the signaling of various processes in the body. As such, in addition to high levels of protein, certain patient groups may require administration of nutritional compositions having increased levels of anti-oxidant nutrients, especially vitamins C and E as well as beta-carotene to help control the excessive formation of free radicals.

Similarly, a lack of protein can also damage diaphragm muscle mass. For example, a ventilator-managed patient may develop atrophy of the diaphragm due to the lack of exertion during breathing. Maintaining the protein content of this muscle may allow for more rapid weaning from a ventilator. As a result of ventilator-weaning, providing adequate protein content to such patients can reduce the amount of healthcare costs incurred by the patient, as well as healthcare providers.

Even in a situation where adequate protein is, in fact, provided by modular products of the prior art, cost and staff time can be consumed in the preparation and administration of multiple modular products. Additionally, the patient may also be at increased risk of developing an infection due to the handling of the modular products and the use of the feeding system. If infection does occur due to a compromised gastrointestinal tract, or any other reason (e.g., compromised immune system, etc.), the patient will be required to stay in the hospital longer, which will also increase healthcare costs. As such, it is important to ensure that enteral and parenteral patients are provided with diets having adequate amounts of protein, while also avoiding complications associated with overfeeding.

Applicants have surprisingly found that the nutritional compositions of the present disclosure provide a formula that allows for economic efficiency in delivery of care to an enterally-fed patient and provides a high level of protein, while avoiding the complications described above. Indeed, the present nutritional compositions include both the protein necessary to maintain lean body mass, as well as the necessary fatty acid profile to reduce inflammation resulting from the fatty acid profile of administered drugs such as, for example, propofol, and to reduce complications associated with overfeeding an enterally-fed patient treated with similar drugs.

The nutritional compositions of the present disclosure include increased amounts of protein. In an embodiment, the nutritional compositions comprise a source of protein that provides increased amounts of protein. The protein source may be dietary protein including, but not limited to animal protein (such as milk protein, meat protein or egg protein), vegetable protein (such as soy protein, wheat protein, rice protein, and pea protein), or combinations thereof. In an embodiment, the protein is selected from the group consisting of whey, chicken, corn, caseinate, wheat, flax, soy, carob, pea or combinations thereof The skilled artisan will appreciate that the protein content of the present nutritional compositions should be higher than typical enteral formulations. For example, the Recommended Dietary Allowance ("RDA") of protein for both men and women is 0.80 g of good quality protein/kg body weight/day and is based on careful analysis of available nitrogen balance studies. See, National Academy of Sciences, Institute of Medicine, Food and Nutrition Board, "Dietary Reference Intakes for Energy, Carbohydrate, Fiber, Fat, Fatty Acids, Cholesterol, Protein, and Amino Acids (Macronutrients)," Chapter 10 (2005). In an embodiment, the present compositions may provide protein to a patient in an amount that is nearly twice the RDA of protein for men and women.

In an example, the nutritional compositions may be provided with a total energy content of 1150 kcal, which may contain about 106 g protein. With the 2009 American Society for Parenteral and Enteral Nutrition ("ASPEN") guidelines stating that at least 2.0 g/kg ideal body weight ("IBW") be provided to patients with a body mass index ("BMI") up to 39, the present nutritional compositions will provide enough protein even if the feeding volume is reduced to accommodate the increased calories provided by a propofol infusion.

In an embodiment, the nutritional compositions of the present disclosure provide at least 30% of its energy as protein. In another embodiment, the nutritional compositions of the present disclosure provide at least 35% of its energy as protein. In yet another embodiment, the nutritional compositions of the present disclosure provide at least 37% of its energy as protein. In the embodiment wherein the nutritional compositions of the present disclosure provide at least 37% of its energy as protein, the nutritional composition contains about 140 g of protein per 1500 kcal, and meets 2009 ASPEN guidelines for feeding obese patients. As such, in an embodiment, the nutritional compositions are formulated for administration to obese patients.

Depending on the weight of the patient, and the desired amount of energy from protein to be provided to the patient, the skilled artisan will appreciate that the amounts of protein administered to a patient per day may vary. For example, the amount of protein administered per day to a patient may range from about 50 g to about 200 g. In an embodiment, the amount of protein administered per day to a patient may range from about 75 g to about 150 g. In an embodiment, the amount of protein administered per day to a patient may be about 140 g. The protein may be administered per 1500 kcal of nutritional composition. The source of protein may provide protein in an amount from about 100 g to about 150 g per 1150 kcal of nutritional composition. The source of protein may provide protein in an amount of about 106 g per 1150 kcal. The Example provided below further illustrate how amounts of protein may be calculated depending on the weight of the patient and the desired amount of energy from protein to be provided to the patient.

The nutritional compositions of the present disclosure may also include fish oil and/or a source of fish oil. The fish oil may be a source of omega-3 fatty acids selected from the group consisting of eicosapentaenoic acid ("EPA"), docosahexaenoic acid ("DHA"), and combinations thereof. Regardless of the amount of fish oil included in the nutritional compositions, the compositions should have a low ratio of omega-6 to omega-3 fatty acids. For example, and in an embodiment, the nutritional compositions include a ratio of omega-6:omega-3 fatty acids from about 1.0:0.5 to about 2.5:1.5. In an embodiment, the nutritional compositions have a ratio of omega-6:omega-3 fatty acids of about 1.8:1.0.

Even with the administration of, for example, up to 40 g/day of soybean oil with a propofol administration, the omega-6:omega-3 ratio with a full day of feeding with the present nutritional compositions would be about 4.1:1. If a patient requires less amounts of the nutritional compositions, a 20% reduction in the amount administered over a day would only give an omega-6:omega-3 ratio for that day of less than about 5:1.

In an embodiment, the present nutritional compositions include an increased amount of protein in combination with a fish oil, and the composition includes a low ratio of omega-6:omega-3 fatty acids. Such a combination can drastically reduce, if not eliminate, excessive inflammation that results from the use of propofol. The combination can also drastically reduce, if not eliminate, any complications associated with overfeeding in an effort to administer adequate amounts of protein to a patient.

The nutritional compositions can include an increased amount of medium-chain triglycerides ("MCTs") to minimize the amount of linoleic acid while still meeting essential fatty acid requirements. MCTs are medium-chain (6 to 12 carbons) fatty acid esters of glycerol. MCTs passively diffuse from the gastrointestinal tract to the portal system (longer fatty acids are absorbed into the lymphatic system) without requirement for modification like long-chain fatty acids or very-long-chain fatty acids. In addition, MCTs do not require bile salts for digestion.

The nutritional compositions may also include a source of fiber, fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber. In an embodiment, the fiber is a probiotic fiber that is capable of promoting the growth of beneficial microbes as part of the microbiota. This will induce a reduction in colonic pH which, in turn, can cause a reduction in protein putrifcation. This reduction can help to maintain colonic health in the short term since there will be a lower concentration of toxic putricens and in the long term since the products of putrification are associated with an increased risk of colon cancer.

In an embodiment, the nutritional compositions include a fish oil in combination with a probiotic fiber. This combination can help to minimize the potential to develop gastroporesis and ileus by modulation of inflammation of the gastrointestinal tract. Additionally, with proper movement of chyme through the gastrointestinal tract, bacterial overgrowth is less likely to occur.

In an embodiment, the nutritional composition further includes one or more prebiotics. As used herein, a prebiotic is a selectively fermented ingredient that allows specific changes, both in the composition and/or activity in the gastrointestinal microflora, that confers benefits upon host well-being and health. Non-limiting examples of prebiotics include acacia gum, alpha glucan, arabinogalactans, beta glucan, dextrans, fructooligosaccharides, galactooligosaccharides, galactomannans, gentiooligosaccharides, glucooligosaccharides, guar gum, inulin, isomaltooligosaccharides, lactosucrose, lactulose, levan, maltodextrins, partially hydrolyzed guar gum, pecticoligosaccharides, retrograded starch, soyoligosaccharides, sugar alcohols, xylooligosaccharides, or a combination thereof In an embodiment, the nutritional composition further includes one or more probiotics. As used herein, probiotics are defined as microorganisms (e.g., dead or live) that could confer health benefits on the host when administered in adequate amounts. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or a combination thereof.

In an embodiment, the nutritional composition further includes a source of carbohydrates. Any suitable carbohydrate may be used in the present nutritional compositions including, but not limited to, sucrose, lactose, glucose, fructose, corn syrup solids, maltodextrin, modified starch, amylose starch, tapioca starch, corn starch or combinations thereof In an embodiment, the nutritional compositions further include a source of fat. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like) and animal fats (such as milk fat).

In another embodiment, the nutritional composition further includes one or more amino acids. Non-limiting examples of amino acids include isoleucine, alanine, leucine, asparagine, lysine, aspartate, methionine, cysteine, phenylalanine, glutamate, threonine, glutamine, tryptophan, glycine, valine, proline, serine, tyrosine, arginine, histidine or combinations thereof.

In an embodiment, the nutritional composition further includes one or more synbiotics, phytonutrients and/or antioxidants. As used herein, a synbiotic is a supplement that contains both a prebiotic and a probiotic that work together to improve the microflora of the intestine. Non-limiting examples of phytonutrients include flavonoids and allied phenolic and polyphenolic compounds, terpenoids such as carotenoids, and alkaloids; including curcumin, limonin, and quercetin. As used herein the term "antioxidant" is preferably understood to include any one or more of various substances (as beta-carotene (a vitamin A precursor), vitamin C, vitamin E, and selenium) that inhibit oxidation or reactions promoted by Reactive Oxygen Species (ROS) and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (Wolfberry), hesperidine, Lactowolfberry, lignan, lutein, lycopene, polyphenols, selenium, vitamin A, vitamin B1, vitamin B6, vitamin B12, vitamin C, vitamin D, vitamin E, or combinations thereof.

In an embodiment, the nutritional composition further includes one or more vitamins and minerals. Non-limiting examples of vitamins include Vitamins A, B-complex (such as B-1, B-2, B-6 and B-12), C, D, E and K, niacin and acid vitamins such as pantothenic acid and folic acid, biotin, or combinations thereof. Non-limiting examples of minerals include calcium, iron, zinc, magnesium, iodine, copper, phosphorus, manganese, potassium, chromium, molybdenum, selenium, nickel, tin, silicon, vanadium, boron, or combinations thereof Other optional ingredients can be added to make the nutritional composition sufficiently palatable. For example, the nutritional compositions of the present disclosure can optionally include conventional food additives, such as any of, acidulants, additional thickeners, buffers or agents for pH adjustment, chelating agents, colorants, emulsifiers, excipient, flavor agent, mineral, osmotic agents, a pharmaceutically acceptable carrier, preservatives, stabilizers, sugar, sweeteners, texturizers, or combinations thereof. The optional ingredients can be added in any suitable amount.

Applicants have surprisingly found that the nutritional compositions of the present disclosure provide a formula that allows for economic efficiency in delivery of care to the patient and provides a high level of protein, while avoiding the overfeeding complications described above. Indeed, the present nutritional compositions include both the protein necessary to maintain lean body mass, as well as the necessary fatty acid profile to reduce inflammation due to the pro-inflammatory fatty acid profile of certain administered drugs such as, for example, propofol.

As discussed herein, the present nutritional compositions may include high amounts of protein and may be suited for, for example, administration to obese, critically ill patients, and/or enterally-fed patients being treated with propofol. The administration of such nutritional compositions can result in benefits and advantages including, among others, reduced gastroparesis, reduced risk of ileus, reduced bacterial overgrowth, reduced bacterial translation, decreased infections, decreased $CO_2$ production, decreased time on a ventilator, decreased metabolic acidosis, decreased respiratory acidosis, decreased ventilator weaning time, reduced hypotension, decreased length of stay in a healthcare clinic or hospital, decreased healthcare costs, and decreased labor time for healthcare professionals. A further advantage of the present nutritional compositions is decreased liver toxicities. Indeed, the administration of adequate amounts of protein supports hepatic function and detoxification of administered drugs. While avoiding overfeeding, the liver is less likely to become enlarged with diffuse fat deposits.

The skilled artisan will appreciate that the use of the present nutritional compositions with patients receiving propofol is not the only possible use for the nutritional compositions of the present disclosure. As such, the skilled artisan can potentially expand the market for this product beyond its indicated use. Indeed, the skilled artisan will appreciate that the present nutritional compositions may be used with any known drug formulations that provide high amounts of calories and/or fats and could benefit from a reformulation of the protein/fat content. These formulations may be reformulated, for example, to provide high-protein, low-fat formulations to avoid complications associated with overfeeding.

By way of example and not limitation, the following Example is illustrative of nutritional compositions in accordance with the present disclosure.

EXAMPLE

The nutritional compositions of the present disclosure are capable of providing many benefits to, for example, an enterally fed patient. As discussed above, the nutritional compositions may be formulated for administration to an obese patient. As such, this Example is directed to a nutritional composition formulated for an obese patient.

A typical obese critical care patient generally has the following physical statistics:

Male, 60 years of age with a body mass index of 35, height of about 180 cm, and weight of about 113.4 kg (250 lbs). The patient's ideal body weight ("IBW") is about 68.4 kg (150.79 lbs). The patient's target energy requirements/basal metabolic rate ("BMR") is about 2111.6 kcal.

Three methods for establishing the caloric needs of the patient are:

1) 60-70% of BMR, which estimates a caloric feeding goal of 1267-1478 kcal;

2) 11-14 kcal/kg actual body weight ("ABW"), which estimates a caloric feeding goal of 1248-1587 kcal; and 3) 22-25 kcal/kg IBW, which estimates a caloric feeding goal of 1505-1710 kcal.

The protein requirement is estimated at 2.0 g/kg IBW, which estimates as 2.0 g×68.4 kg=136.8 g.

These three methods of estimating caloric needs give an average daily caloric goal of 1466 kcal. Since closed system products are available in 1.0 and 1.5 liter containers, a caloric density of 1.0 kcal/mL is a logical formulation goal for this formula.

As the degree of obesity decreases, the need to deliver this higher level of protein also decreases. Thus, the use of this formula in patients sedated with propofol delivers adequate amounts of protein that are required by most patients.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of reducing the fat intake of a patient being treated with, or having been treated with, a high fat medication, the method comprising:
    providing an effective amount of an enteral nutritional composition comprising protein in an amount of at least 30% of the total energy of the nutritional composition, and a source of fatty acids that provides the nutritional composition with an omega-6 to omega-3 fatty acid ratio from about 1.0:0.5 to about 2.5:1.5; and
    administering the nutritional composition to the patient daily and for a short-term.

2. The method according to claim 1, wherein the ratio of omega-6:omega-3 fatty acids is about 1.8:1.0.

3. The method according to claim 1, wherein the protein comprises at least 35% of the total energy of the nutritional composition.

4. The method according to claim 1, wherein the patient is a mechanically ventilated patient.

* * * * *